(12) United States Patent
Cannon et al.

(10) Patent No.: US 7,368,530 B2
(45) Date of Patent: May 6, 2008

(54) HUMAN INTESTINAL NPT2B

(75) Inventors: Paul David Cannon, San Carlos, CA (US); Suryanarayana Sankuratri, San Mateo, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 1341 days.

(21) Appl. No.: 10/052,664

(22) Filed: Jan. 17, 2002

(65) Prior Publication Data

US 2002/0156266 A1    Oct. 24, 2002

Related U.S. Application Data

(63) Continuation-in-part of application No. 09/499,964, filed on Feb. 28, 2000, now Pat. No. 6,380,374.

(60) Provisional application No. 60/119,321, filed on Feb. 9, 1999.

(51) Int. Cl.
C07K 1/00 (2006.01)
C07K 14/00 (2006.01)
C07K 17/00 (2006.01)

(52) U.S. Cl. ................................... 530/350
(58) Field of Classification Search ............... 530/350, 530/300

See application file for complete search history.

(56) References Cited

U.S. PATENT DOCUMENTS 5,985,604 A    11/1999   Lal et al. ................... 435/69.1
6,319,688 B1   11/2001   Feild

FOREIGN PATENT DOCUMENTS

EP    0 875 569 A1    9/1998

OTHER PUBLICATIONS

Xu et al. Genomics, 1999, 62: 281-284.*
Bork et al, Predicting functions from protein sequences-where are the bottlnecks, Nature Genetics, vol. 18, pages 313-318, 1998.*
Karp, Peter D. Editorial, Bioinformatics, vol. 14, No. 9, pp. 753-754, 1998.*
Bork, Peter, sequences and topology deriving biological knowledge from genomic sequences,, current Opinion in Structural biology, vol. 8, pp. 331-332, 1998.*
Hilfiker et al,; "Characterization of a murine type II sodium-phosphate contransporter expressed in mammalian small intentine"; Proc. Natl. Acad. Sci. USA; vol. 95, pp. 14564-14569, Nov. 1998; Physiology.
Magagnin et al.; "Expression cloning of human and rat renal cortex Na/Pi cotransport"; Proc. Natl. Acad. Sci, USA; vol. 90, pp. 5979-5983; Jul. 1993; Biochemistry.
Hohl et al.; "Na-Pi cotransport in flounder: same transport system in kidney and intestine" 1996 the American Physiological Society; pp. F937-f944 (1966).
Atsuko Ishizuya-Oka, et al., "Temporal and Spatial Expression of An Intestinal Na+PO$_4$3- Cotransporter Correlates With Epithelial Hormone-Dependent Frog Metamorphosis," *Development Genetics*, (1997) pp. 53-66, vol. 20.
John A. Field, et al.; "Cloning and Functional Characterization of a Sodium-Dependent Phosphate Transporter Expressed in Human Lung and Small Intestine," Biochemical and Biophysical Research Communications, (1999) pp. 578-582, vol. 258.
Kenneth E. White, et al.,"Chromosomal Localization of Two Human Genes Involved in Phosphate Homeostasis: The Type 1lb Sodium-Phosphate Cotransporter and Stanniocalcin-2," Somatic Cell and Molecular Genetics, (1998) pp. 357-362, vol. 24:6.
Hua Xu, et al., "Molecular Cloning, Functional Characterization, Tissue Distribution, and Chromosomal Localization of a Human, Small Intestinal Sodium-Phosphate Transporter," Genomics, (1999) pp. 281-284, vol. 62:2.

* cited by examiner

*Primary Examiner*—Christine J. Saoud
*Assistant Examiner*—Nirmal Singh Basi
(74) *Attorney, Agent, or Firm*—David J. Chang

(57) ABSTRACT

A novel human sodium phosphate cotransporter expressed on the apical surface of intestinal epithelial cells (huNpt2B) and polypeptides related thereto, as well as nucleic acid compositions encoding the same, are provided. The subject polypeptides and nucleic acid compositions find use in a variety of applications, including research, diagnostic, and therapeutic agent screening applications. Also provided are methods of inhibiting Npt2B activity in a host and methods of treating disease conditions associated with Npt2B activity.

1 Claim, 3 Drawing Sheets

FIG. 1

```
  1  MAPWPELGDA QPNPDKYLEG AAGQQPTAPD KSKETNKNNT EAPVTKIELL
 51  PSYSTATLID EPTEVDDPWN LPTLQDSGIK WSERDTKGKI LCFFQGIGRL
101  ILLLGFLYFF VCSLDILSSA FQLVGGKMAG QFFSNSSIMS NPLLGLVIGV
151  LVTVLVQSSS TSTSIVVSMV SSSLLTVRAA IPIIMGANIG TSITNTIVAL
201  MQVGDRSEFR RAFAGATVHD FFNWLSVLVL LPVEVATHYL EIITQLIVES
251  FHFKNGEDAP DLLKVITKPF TKLIVQLDKK VISQIAMNDE KAKNKSLVKI
301  WCKTFTNKTQ INVTVPSTAN CTSPSLCWTD GIQNWTMKNV TYKENIAKCQ
351  HIFVNFHLPD LAVGTILLIL SLLVLCGCLI MIVKILGSVL KGQVATVIKK
401  TINTDFPFPF AWLTGYLAIL VGAGMTFIVQ SSSVFTSALT PLIGIGVITI
451  ERAYPLTLGS NIGTTTTAIL AALASPGNAL RSSLQIALCH FFFNISGILL
501  WYPIPFTRLP IRMAKGLGNI SAKYRWFAVF YLIIFFFLIP LTVFGLSLAG
551  WRVLVGVGVP VVFIIILVLC LRLLQSRCPR VLPKKLQNWN FLPLWMRSLK
601  PWDAVVSKFT GCFQMRCCCC CRVCCRACCL LCGCPKCCRC SKCCEDLEEA
651  QEGQDVPVKA PETFDNITIS REAQGEVPAS DSKTECTAL*  (SEQ ID NO:01)
```

FIG. 2A

```
   1 CTGACGTAGG CCCAGCACCT GCGGAGGGAG CGCTGACCAT GGCTCCCTGG
  51 CCTGAATTGG GAGATGCCCA GCCCAACCCC GATAAGTACC TCGAAGGGGC
 101 CGCAGGTCAG CAGCCCACTG CCCCTGATAA AAGCAAAGAG ACCAACAAAA
 151 ATAACACTGA GGCACCTGTA ACCAAGATTG AACTTCTGCC GTCCTACTCC
 201 ACGGCTACAC TGATAGATGA GCCCACTGAG GTGGATGACC CCTGGAACCT
 251 ACCCACTCTT CAGGACTCGG GGATCAAGTG GTCAGAGAGA GACACCAAAG
 301 GGAAGATTCT CTGTTTCTTC CAAGGGATTG GGAGATTGAT TTTACTTCTC
 351 GGATTTCTCT ACTTTTTCGT GTGCTCCCTG GATATTCTTA GTAGCGCCTT
 401 CCAGCTGGTT GGAGGAAAAA TGGCAGGACA GTTCTTCAGC AACAGCTCTA
 451 TTATGTCCAA CCCTTTGTTG GGGCTGGTGA TCGGGGTGCT GGTGACCGTC
 501 TTGGTGCAGA GCTCCAGCAC CTCAACGTCC ATCGTTGTCA GCATGGTGTC
 551 CTCTTCATTG CTCACTGTTC GGGCTGCCAT CCCCATTATC ATGGGGGCCA
 601 ACATTGGAAC GTCAATCACC AACACTATTG TTGCGCTCAT GCAGGTGGGA
 651 GATCGGAGTG AGTTCAGAAG AGCTTTTGCA GGAGCCACTG TCCATGACTT
 701 CTTCAACTGG CTGTCCGTGT TGGTGCTCTT GCCCGTGGAG GTGGCCACCC
 751 ATTACCTCGA GATCATAACC CAGCTTATAG TGGAGAGCTT CCACTTCAAG
 801 AATGGAGAAG ATGCCCCAGA TCTTCTGAAA GTCATCACTA AGCCCTTCAC
 851 AAAGCTCATT GTCCAGCTGG ATAAAAAAGT TATCAGCCAA ATTGCAATGA
 901 ACGATGAAAA AGCGAAAAAC AAGAGTCTTG TCAAGATTTG GTGCAAAACT
 951 TTTACCAACA AGACCCAGAT TAACGTCACT GTTCCCTCGA CTGCTAACTG
1001 CACCTCCCCT TCCCTCTGTT GGACGGATGG CATCCAAAAC TGGACCATGA
1051 AGAATGTGAC CTACAAGGAG AACATCGCCA AATGCCAGCA TATCTTTGTG
1101 AATTTCCACC TCCCGGATCT TGCTGTGGGC ACCATCTTGC TCATACTCTC
1151 CCTGCTGGTC CTCTGTGGTT GCCTGATCAT GATTGTCAAG ATCCTGGGCT
1201 CTGTGCTCAA GGGGCAGGTC GCCACTGTCA TCAAGAAGAC CATCAACACT
1251 GATTTCCCCT TTCCCTTTGC ATGGTTGACT GGCTACCTGG CCATCCTCGT
1301 CGGGGCAGGC ATGACCTTCA TCGTACAGAG CAGCTCTGTG TTCACGTCGG
1351 CCTTGACCCC CCTGATTGGA ATCGGCGTGA TAACCATTGA GAGGGCTTAT
1401 CCACTCACGC TGGGCTCCAA CATCGGCACC ACCACCACCG CCATCCTGGC
1451 CGCCTTAGCC AGCCCTGGCA ATGCATTGAG GAGTTCACTC CAGATCGCCC
1501 TGTGCCACTT TTTCTTCAAC ATCTCCGGCA TCTTGCTGTG GTACCCGATC
1551 CCGTTCACTC GCCTGCCCAT CCGCATGGCC AAGGGGCTGG GCAACATCTC
1601 TGCCAAGTAT CGCTGGTTCG CCGTCTTCTA CCTGATCATC TTCTTCTTCC
1651 TGATCCCGCT GACGGTGTTT GGCCTCTCGC TGGCCGGCTG GCGGGTGCTG
1701 GTTGGTGTCG GGGTTCCCGT CGTCTTCATC ATCATCCTGG TACTGTGCCT
1751 CCGACTCCTG CAGTCTCGCT GCCCACGCGT CCTGCCGAAG AAACTCCAGA
1801 ACTGGAACTT CCTGCCGCTG TGGATGCGCT CGCTGAAGCC CTGGGATGCC
1851 GTCGTCTCCA AGTTCACCGG CTGCTTCCAG ATGCGCTGCT GCTGCTGCTG
1901 CCGCGTGTGC TGCCGCGCGT GCTGCTTGCT GTGTGGCTGC CCCAAGTGCT
1951 GCCGCTGCAG CAAGTGCTGC GAGGACTTGG AGGAGGCGCA GGAGGGGCAG
2001 GATGTCCCTG TCAAGGCTCC TGAGACCTTT GATAACATAA CCATTAGCAG
2051 AGAGGCTCAG GGTGAGGTCC CTGCCTCGGA CTCAAAGACC GAATGCACGG
2101 CCTTGTAGGG GACGCCCCAG ATTGTCAGGG ATGGGGGGAT GGTCCTTGAG
2151 TTTTGCATGC TCTCCTCCCT CCCACTTCTG CACCCTTTCA CCACCTCGAG
2201 GAGATTTGCT CCCCATTAGC GAATGAAATT GATGCAGTCC TACCTAACTC
2251 GATTCCCTTT GGCTTGGTGG GTAGGCCTGC AGGGCACTTT TATTCCAACC
2301 CCTGGTCACT CAGTAATCTT TTACTCCAGG AAGGCACAGG ATGGTACCTA
2351 AAGAGAATTA GAGAATGAAC CTGGCGGGAC GGATGTCTAA TCCTGCACCT
2401 AGCTGGGTTG GTCAGTAGAA CCTATTTTCA GACTCAAAAA CCATCTTCAG
2451 AAAGAAAAGG CCCAGGGAAG GAATGTATGA GAGGCTCTCC CAGATGAGGA
2501 AGTGTACTCT CTATGACTAT CAAGCTCAGG CCTCTCCCTT TTTTAAACC
2551 AAAGTCTGGC AACCAAGAGC AGCAGCTCCA TGGCCTCCTT GCCCCAGATC
2601 AGCCTGGGTC AGGGGACATA GTGTCATTGT TTGGAAACTG CAGACCACAA
```

FIG. 2B

```
2651 GGTGTGGGTC TATCCCACTT CCTAGTGCTC CCCACATTCC CCATCAGGGC
2701 TTCCTCACGT GGACAGGTGT GCTAGTCCAG GCAGTTCACT TGCAGTTTCC
2751 TTGTCCTCAT GCTTCGGGGA TGGGAGCCAC GCCTGAACTA GAGTTCAGGC
2801 TGGATACATG TGCTCACCTG CTGCTCTTGT CTTCCTAAGA GACAGAGAGT
2851 GGGGCAGATG GAGGAGAAGA AAGTGAGGAA TGAGTAGCAT AGCATTCTGC
2901 CAAAAGGGCC CCAGATTCTT AATTTAGCAA ACTAAGAAGC CCAATTCAAA
2951 AGCATTGTGG CTAAAGTCTA ACGCTCCTCT CTTGGTCAGA TAACAAAAGC
3001 CCTCCCTGTT GGATCTTTTG AAATAAAACG TGCAAGTTAT CCAGGCTCGT
3051 AGCCTGCATG CTGCCACCTT GAATCCCAGG GAGTATCTGC ACCTGGAATA
3101 GCTCTCCACC CCTCTCTGCC TCCTTACTTT CTGTGCAAGA TGACTTCCTG
3151 GGTTAACTTC CTTCTTTCCA TCCACCCACC CACTGGAATC TCTTTCCAAA
3201 CATTTTTCCA TTTTCCCACA GATGGGCTTT GATTAGCTGT CCTCTCTCCA
3251 TGCCTGCAAA GCTCCAGATT TTTGGGGAAA GCTGTACCCA ACTGGACTGC
3301 CCAGTGAACT GGGATCATTG AGTACAGTCG AGCACACGTG TGTGCATGGG
3351 TCAAAGGGGT GTGTTCCTTC TCATCCTAGA TGCCTTCTCT GTGCCTTCCA
3401 CAGCCTCCTG CCTGATTACA CCACTGCCCC CGCCCCACCC TCAGCCATCC
3451 CAATTCTTCC TGGCCAGTGC GCTCCAGCCT TATCTAGGAA AGGAGGAGTG
3501 GGTGTAGCCG TGCAGCAAGA TTGGGGCCTC CCCCATCCCA GCTTCTCCAC
3551 CATCCCAGCA AGTCAGGATA TCAGACAGTC CTCCCCTGAC CCTCCCCCTT
3601 GTAGATATCA ATTCCCAAAC AGAGCCAAAT ACTCTATATC TATAGTCACA
3651 GCCCTGTACA GCATTTTTCA TAAGTTATAT AGTAAATGGT CTTCTAGTGC
3701 TCTCATTTGG AAATGAGGCA GGCTTCTTCT ATGAAATGTA AAGAAAGAAA
3751 CCACTTTGTA TATTTTGTAA TACCACCTCT GTGGCCATGC CTGCCCCGCC
3801 CACTCTGTAT ATATGTAAGT TAAACCCGGG CAGGGGCTGT GGCCGTCTTT
3851 GTACTCTGGT GATTTTAGA AATTGAATCT TTGTACTTGC ATTGATTGTA
3901 TAATAATTTT GAGACCAGGT CTCGCTGTGT TGCTCAGGCT GGTCTCAAAC
3951 TCCTGAGATC AAGCAATCCG CCCACCTCAG CCTCCCAAAG TGCTGAGATC
4001 ACAGGCGTGA GCCACCACCA GGCCTGATTG TAATTTTTTT TTTTTTTTT
4051 TTTACTGGTT ATGGGAAGGG AGAAATAAAA TCATCAAACC CAAAAAAAA
4101 AAAAAAAAAA AAAAAAAAAA AAAAAAAAAA AAAAAAA     (SEQ ID NO:02)
```

HUMAN INTESTINAL NPT2B

CROSS REFERENCE TO RELATED APPLICATIONS

This application is a divisional application of U.S. patent application Ser. No. 09/499,964, filed Feb. 8, 2000, now U.S. Pat. No. 6,380,374, which application claims priority to the filing date of the U.S. Provisional Patent Application Ser. No. 60/119,321 filed Feb. 9, 1999, the disclosures of which are herein incorporated by reference.

INTRODUCTION

1. Field of the Invention

The field of the invention is ion transporters, particularly sodium phosphate co-transporters.

2. Background of the Invention

Phosphorous plays an important role in membrane structure, transport and energy storage. At normal physiological pH (e.g. pH of 7.4), inorganic phosphate (Pi) in plasma is made up of a 4:1 mixture of $HPO_4^{2-}$ and $H_2PO_4^-$. Of the 700 g of phosphorous present in the body, 0.1% is present in the extracellular fluid in a freely diffusible form. The plasma level of Pi is maintained through control of Pi absorption in the small intestine, under the influence of vitamin D, and Pi excretion in the kidney, under the influence of parathyroid hormone.

Absorption of Pi requires transepithelial transport. A critical step of transepithelial transport of Pi is the uptake of Pi into epithelial cells. Pi uptake is accomplished by sodium phosphate co-transporters present on the apical surface of appropriate epithelial cells, e.g. intestinal and renal epithelial cells. A variety of sodium phosphate co-transporters have been identified to date, including: NaPi-1 (rabbit); NPT1 (human); Npt1 (mouse); NaPi-2 (rat); NaPi-3 (human); NaPi-4 (opossum); NaPi-5 (flounder); NaPi-6 (rabbit); NaPi-7 (mouse); and NaPi of NBL-1 cells (bovine).

A variety of disease conditions are associated with disorders in Pi metabolism, where such disease conditions include those characterized by the presence of hypophosphatemia, e.g. osteomalacia, hypocalciuria and rickets, and those characterized by the presence of hyperphosphatemia, e.g. hyperparathyroidism, hypocalcemia, vitamin D deficiency, soft tissue or metastatic calcification, and the like. In particular, hyperphosphatemia is a characteristic of renal disease and failure, and is an underlying cause of many of the deleterious symptoms observed with such renal complications.

Methods of treating abnormalities in Pi metabolism are varied. For example, for disease conditions associated with the presence of hypophosphatemia, treatment methodologies include: changes in diet to include phosphorous rich foods, supplementation with phosphorous salts, use of therapeutic agents, e.g. dipyridamole, and the like. For those disease conditions associated with hyperphosphatemia, treatment in the absence of renal insufficiency may include hydration and/or the use of aluminum based antacids that bind phosphorous in the intestinal lumen. Where renal insufficiency is present, phosphate binders and/or dietary modification to restrict phosphorous intake are potentially useful, but dialysis is typically employed.

Because of the wide variety of disease conditions characterized by the presence of abnormal Pi metabolism, there is continued interest in the identification of the molecular components responsible for Pi metabolism. Of particular interest would be the identification of the intestinal transporter responsible for absorption and uptake of Pi in the intestine.

Relevant Literature

Hilfiker et al., Proc. Nat'l Acad. Sci. USA (1998) 95:14564-14569 discloses the mouse Npt2B nucleic acid sequence. Also of interest is: Feild et al., "Cloning and Characterization of a Sodium Dependent Phosphate Transporter Isoform Expressed in Human Small Intestine and Lung," Published on Dec. 24, 1998 under GenBank Accession No. 4071357 and submitted by Smithkline Beecham Pharmaceuticals, 709 Swedeland Road, King of Prussia, PA 19406 on Dec. 7, 1998). References disclosing sodium phosphate co-transporters include: Werner et al., Proc. Nat'l Acad. Sci. USA (1991) 88: 9608-9612; Chong et al., Genomics (1993) 18:355-359; Chong et al., Am. J. Physiol. (1995) 268: F1038-F1045; Magagnin et al., Proc. Nat'l Acad. Sci. USA (1993) 90:5979-5983; Sorribas et al., J. Biol. Chem. (1994) 269:6615-6621; Werner et al., Am. J. Physiol. (1995) 267: F311-F317; Verri et al., Am J. Physiol. (1995) 268:F626-F633; Collins et al., FASEB J. (1994) 8:862-868; and Helps et al., Eur. J. Biochem. (1995) 228: 927-930.

Also of interest is WO 98/37198.

References providing background information on the role of sodium phosphate co-transporters in phosphorous metabolism include: Tenenhouse, J. Bone Min. Res. (1997) 12: 159; and Harrison's Principles of Internal Medicine, $14^{th}$ Ed. (1998) pp2259-2263.

SUMMARY OF THE INVENTION

A novel human intestinal sodium phosphate co-transporter (i.e. Npt2B) and polypeptides related thereto, as well as nucleic acid compositions encoding the same, are provided. The subject polypeptide and nucleic acid compositions find use in a variety of applications, including research, diagnostic, and therapeutic agent screening applications, as well as in treatment therapies. Also provided are methods of treating disease conditions associated with intestinal Npt2B function, e.g. conditions characterized by abnormal serum phosphate levels, such as hypo- and hyperphosphatemia.

BRIEF DESCRIPTION OF THE DRAWINGS

FIG. 1 provides the amino acid sequence of human Npt2B.

FIG. 2 provides the sequence of a nucleic acid encoding human Npt2B.

DETAILED DESCRIPTION OF THE INVENTION

A novel human intestinal sodium phosphate co-transporter (i.e. Npt2B) and polypeptides related thereto, as well as nucleic acid compositions encoding the same, are provided. The subject polypeptide and/or nucleic acid compositions find use in a variety of different applications, including research, diagnostic, and therapeutic agent screening/discovery/preparation applications. Also provided are methods of treating disease conditions associated with intestinal Npt2B function, e.g. conditions resulting in abnormal serum phosphate levels, such as hypo- and hyperphosphatemia.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Polypeptide Compositions

A novel human sodium phosphate co-transporter expressed in intestinal epithelial cells, as well as polypeptide compositions related thereto, are provided. The term polypeptide composition as used herein refers to both the full length human protein as well as portions or fragments thereof. Also included in this term are variations of the naturally occurring human protein, where such variations are homologous or substantially similar to the naturally occurring protein, as described in greater detail below. In the following description of the subject invention, the term Npt2B is used to refer to the wild type human intestinal sodium phosphate co-transporter molecule of the subject invention.

The Npt2B protein of the subject invention is a membrane protein having a number of transmembrane regions, where the number of putative transmembrane regions based on the amino acid sequence is 10 (as predicted using TMpred (www.Ch.embnet.org) based on TMbase (Tmbase-Adatabase of membrane spanning protein segments. Biol. Chem. Hoppe-Seyler 347, 166)). Npt2B is a type II sodium phosphate co-transporter. In its native environment, Npt2B is a co-transporter of sodium cation and phosphate anion. Npt2B is expressed, among other locations, on the surface of intestinal epithelial cells, i.e. on the apical or intestinal luminal side of the epithelial cells, and therefore provides for the transport of sodium and phosphate ions from the intestinal lumen into the intestinal epithelial cells. Npt2b is also expressed in lung type II alveolar cells where it may be involved in transport of phosphate into the cells to meet the increased demand for mucin glycoprotein synthesis. Npt2B has a 23% amino acid sequence identity with human NPT1 as described in Chong et al., "Molecular cloning of the cDNA encoding a human renal sodium phosphate transport protein and its assignment to chromosome 6p21.3-p23," Genomics (1993)18: 355-359 and 52.5% identity to human Npt2a described in Maganin et al. "Expression Cloning of Human and Rat Renal Cortex Na/Pi co-transport," Proc. Natl. Acad. Sci. USA (1993) 90: 5979-5983 (as measured by MegAlign, DNAstar (1998) using clustal algoritm as described in D. G. Higgins and P. M. Sharp. Fast and Sensitive multiple Sequence Alignments on a Microcomputer. (1989) CABIOS, 5: 151-153. Prameters used are ktuple 1, gpa penalty 3, window, 5 and diagonals saved 5). Other Npt2B characteristics include: potential glycosylation sites on the extracellular loops.

Npt2B has an amino acid sequence as shown in FIG. 1 and identified as SEQ ID NO:01. Npt2B has a molecular weight based on its amino acid sequence of about 75 kDa, and more specifically 75598.52 dalton (as determined using Protean/DNAstar (1997) as per H. Nakashima et al. The Folding Type of a pProetin is Related to the Amino Acid Composition. J. Biochem (Tokyo) 99: 153-162). The true molecular weight of Npt2B may vary due to glycosylation and/or other postranslational modifications. As such, the actual molecular weight of Npt2B is likely to be in the range from about 70 to 130 kDa.

Npt2B homologs or proteins (or fragments thereof) that vary in sequence from the wild type sequence of the subject invention are also provided. By homolog is meant a protein having at least about 35%, usually at least about 40% and more usually at least about 60% amino acid sequence identity to the Npt2B protein of the subject invention, (using MegAlign, DNAstar (1998) using clustal algoritm as described in D. G. Higgins and P. M. Sharp. Fast and Sensitive multiple Sequence Alignments on a Microcomputer. (1989) CABIOS, 5: 151-153. Prameters used are ktuple 1, gpa penalty 3, windows 5 and diagonals saved 5).

Also provided are Npt2B proteins that are substantially identical to the hu Npt2B protein, where by substantially identical is meant that the protein has an amino acid sequence identity to the sequence of Npt2B of at least about 60%, usually at least about 65% and more usually at least about 70%.

The proteins of the subject invention are present in a non-naturally occurring environment, e.g. are separated from their naturally occurring environment. In certain embodiments, the subject proteins are present in a composition that is enriched for subject protein as compared to its naturally occurring environment. For example, purified Npt2B is provided, where by purified is meant that Npt2B is present in a composition that is substantially free of non-Npt2B proteins, where by substantially free is meant that less than 90%, usually less than 60% and more usually less than 50% of the composition is made up of non-Npt2B proteins. The proteins of the subject invention may also be present as an isolate, by which is meant that the protein is substantially free of other proteins and other naturally occurring biologic molecules, such as oligosaccharides, polynucleotides and fragments thereof, and the like, where the term "substantially free" in this instance means that less than 70%, usually less than 60% and more usually less than 50% of the composition containing the isolated protein is some other naturally occurring biological molecule. In certain embodiments, the proteins are present in substantially pure form, where by "substantially pure form" is meant at least 95%, usually at least 97% and more usually at least 99% pure.

In addition to the naturally occurring proteins, polypeptides which vary from the naturally occurring proteins are also provided, e.g. Npt2B polypeptides. By Npt2B polypeptide is meant an amino acid sequence encoded by an open reading frame (ORF) of the gene encoding Npt2B, described in greater detail below, including the full length Npt2B protein and fragments thereof, particularly biologically active fragments and/or fragments corresponding to functional domains, e.g. transmembrane domain, and the like; and including fusions of the subject polypeptides to other proteins or parts thereof. Fragments of interest will typically be at least about 10 aa in length, usually at least about 50 aa in length, and may be as long as 300 aa in length or longer, but will usually not exceed about 1000 aa in length, where the fragment will have a stretch of amino acids that is identical to the subject protein of at least about 10 aa, and usually at least about 15 aa, and in many embodiments at least about 50 aa in length.

The subject proteins and polypeptides may be obtained from naturally occurring sources or synthetically produced. For example, Npt2B is generally derived from epithelial cells of the intestine, but may also be derived from other cell types or tissues in which expression of Npt2B is identified, e.g. lung, etc. The subject proteins may also be derived from synthetic means, e.g. by expressing a recombinant gene encoding protein of interest in a suitable host, as described in greater detail below. Any convenient protein purification procedures may be employed, where suitable protein purification methodologies are described in Guide to Protein Purification, (Deuthser ed.) (Academic Press, 1990). For example, a lysate may prepared from the original source, e.g. intestinal epithelial cells or the expression host, and purified using HPLC, exclusion chromatography, gel electrophoresis, affinity chromatography, and the like.

Nucleic Acid Compositions

Also provided are nucleic acid compositions encoding Npt2B proteins or fragments thereof, as well as the Npt2B homologues of the present invention. By Npt2B nucleic acid composition is meant a composition comprising a sequence of DNA having an open reading frame that encodes Npt2B, i.e. a Npt2B gene, and is capable, under appropriate conditions, of being expressed as Npt2B. Also encompassed in this term are nucleic acids that are homologous or substantially similar or identical to the nucleic acids encoding Npt2B proteins. Thus, the subject invention provides genes encoding the human Npt2B of the subject invention and homologs thereof. The human Npt2B gene has the nucleic acid sequence shown in FIG. 2 and identified as SEQ ID NO:02, infra.

The source of homologous genes may be any species, e.g., primate species, particularly human; rodents, such as rats and mice, canines, felines, bovines, ovines, equines, yeast, nematodes, etc. Between mammalian species, e.g., human and mouse, homologs have substantial sequence similarity, e.g. at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403-10 (using default settings, i.e. parameters w=4 and T=17). The sequences provided herein are essential for recognizing Npt2B-related and homologous proteins, and the nucleic acids encoding the same, in database searches.

Nucleic acids encoding the Npt2B protein and Npt2B polypeptides of the subject invention may be cDNA or genomic DNA or a fragment thereof. The term "Npt2B gene" shall be intended to mean the open reading frame encoding specific Npt2B proteins and polypeptides, and Npt2B introns, as well as adjacent 5' and 3' non-coding nucleotide sequences involved in the regulation of expression, up to about 20 kb beyond the coding region, but possibly further in either direction. The gene may be introduced into an appropriate vector for extrachromosomal maintenance or for integration into a host genome.

The term "cDNA" as used herein is intended to include all nucleic acids that share the arrangement of sequence elements found in native mature mRNA species, where sequence elements are exons and 5' and 3' non-coding regions. Normally mRNA species have contiguous exons, with similarity is calculated based on a reference sequence, which may be a subset of a larger sequence, such as a conserved motif, coding region, flanking region, etc A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215403-10 (using default settings, i. e. parameters w=4 and T=17). The sequences provided herein are essential for recognizing Npt2B-related and homologous proteins, and the nucleic acids encoding the same, in database searches.

Nucleic acids encoding the Npt2B protein and Npt2B polypeptides of the subject invention may be cDNA or genomic DNA or a fragment thereof. The term "Npt2B gene" shall be intended to mean the open reading frame encoding specific Npt2B proteins and polypeptides, and Npt2B introns, as well as adjacent 5' and 3' non-coding nucleotide sequences involved in the regulation of expression, up to about 20 kb beyond the coding region, but possibly further in either direction. The gene may be introduced into an appropriate vector for extrachromosomal maintenance or for integration into a host genome.

The term "cDNA" as used herein is intended to include all nucleic acids that share the arrangement of sequence elements found in native mature mRNA species, where sequence elements are exons and 5' and 3' non-coding regions. Normally mRNA species have contiguous exons, with the intervening introns, when present, being removed by nuclear RNA splicing, to create a continuous open reading frame encoding a Npt2B protein.

A genomic sequence of interest comprises the nucleic acid present between the initiation codon and the stop codon, as defined in the listed sequences, including all of the introns that are normally present in a native chromosome. It may further include 5' and 3' untranslated regions found in the mature mRNA. It may further include specific transcriptional and translational regulatory sequences, such as promoters, enhancers, etc., including about 1 kB, but possibly more, of flanking genomic DNA at either the 5' or 3' end of the transcribed region. The genomic DNA may be isolated as a fragment of 100 kbp or smaller; and substatially free of flanking chromosonal sequence. The genomic DNA flanking the coding region, either 3' or 5', or internal regulatory sequences as transcriptional initiation region, and a transcriptional and translational termination region. These control regions may be native to the Npt2B gene, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

Npt2B proteins and polypeptides may be expressed in prokaryotes or eukaryotes in accordance with conventional ways, depending upon the purpose for expression. For large scale production of the protein, a unicellular organism, such as E. coli, B. subtilis, S. cerevisiae, insect cells in combination with baculovirus vectors, or cells of a higher organism such as vertebrates, particularly mammals, e.g. COS 7 cells, HEK 293, CHO, Xenopus Oocytes, etc., may be used as the expression host cells. In some situations, it is desirable to express the Npt2B gene in eukaryotic cells, where the Npt2B protein will benefit from native folding and post-translational modifications. Small peptides can also be synthesized in the laboratory. Polypeptides that are subsets of the complete Npt2B sequence may be used to identify and investigate parts of the protein important for function.

Uses of the Subject Npt2B Polypeptide and Nucleic Acid Compositions

The subject polypeptide and nucleic acid compositions find use in a variety of different applications, including research, diagnostic, and therapeutic agent screening/discovery/preparation applications, as well as in therapeutic compositions and methods employing the same.

Research Applications

The subject nucleic acid compositions find use in a variety of research applications. Research applications of interest include: the identification of Npt2B homologs; as a source of novel promoter elements; the identification of Npt2B expression regulatory factors; as probes and primers in hybridization applications, e.g. PCR; the identification of expression patterns in biological specimens; the preparation of cell or animal models for Npt2B function; the preparation of in vitro models for Npt2B function; etc.

Homologs of Npt2B are identified by any of a number of methods. A fragment of the provided cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 6×SSC (0.9 M sodium chloride/0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/01.5 mM sodium citrate). Nucleic acids having a region of substantial identity to the provided Npt2B sequences, e.g. allelic variants, genetically altered versions of the gene, etc., bind to the provided Npt2B sequences under stringent hybridization conditions. By using probes, particularly labeled probes of DNA sequences, one can isolate homologous or related genes.

The sequence of the 5' flanking region may be utilized for promoter elements, including enhancer binding sites, that provide for developmental regulation in tissues where Npt2B is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995), *Mol. Med.* 1:194-205; Mortlock et al. (1996), *Genome Res.* 6:327-33; and Joulin and Richard-Foy (1995), *Eur. J. Biochem.* 232: 620-626.

The regulatory sequences may be used to identify cis acting sequences required for transcriptional or translational regulation of Npt2B gene expression, especially in different tissues or stages of development, and to identify cis acting sequences and trans-acting factors that regulate or mediate Npt2B gene expression. Such transcription or translational control regions may be operably linked to a Npt2B gene in order to promote expression of wild type or altered Npt2B or other proteins of interest in cultured cells, or in embryonic, fetal or adult tissues, and for gene therapy.

Small DNA fragments are useful as primers for PCR, hybridization screening probes, etc. Larger DNA fragments, i.e. greater than 100 nt are useful for production of the encoded polypeptide, as described in the previous section. For use in geometric amplification reactions, such as geometric PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The DNA may also be used to identify expression of the gene in a biological specimen. The manner in which one probes cells for the presence of particular nucleotide sequences, as genomic DNA or RNA, is well established in the literature. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of Npt2B gene expression in the sample.

The sequence of a Npt2B gene, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al. (1993), *Biotechniques* 14:22; Barany (1985), *Gene* 37:111-23; Colicelli et al. (1985), *Mol. Gen. Genet.* 199:537-9; and Prentki et al. (1984), *Gene*

29:303-13. Methods for site specific mutagenesis can be found in Sambrook et al., *Molecular Cloning: A Laboratory Manual*, CSH Press 1989, pp. 15.3-15.108; Weiner et al. (1993), *Gene* 126:35-41; Sayers et al. (1992), *Biotechniques* 13:592-6; Jones and Winistorfer (1992), *Biotechniques* 12:528-30; Barton et al. (1990), *Nucleic Acids Res* 18:7349-55; Marotti and Tomich (1989), *Gene Anal. Tech.* 6:67-70; and Zhu (1989), *Anal Biochem* 177:120-4. Such mutated genes may be used to study structure-function relationships of Npt2B, or to alter properties of the protein that affect its function or regulation.

The subject nucleic acids can be used to generate transgenic, non-human animals or site specific gene modifications in cell lines. Transgenic animals may be made through homologous recombination, where the endogenous Npt2B locus is altered. Alternatively, a nucleic acid construct is randomly integrated into the genome. Vectors for stable integration include plasmids, retroviruses and other animal viruses, YACs, and the like.

The modified cells or animals are useful in the study of Npt2B function and regulation. Of interest is the use of Npt2B genes to construct transgenic animal models of Npt2B related disease conditions, e.g. hyper- or hypophosphatemia. Thus, transgenic animal models of the subject invention include endogenous Npt2B knockouts in which expression of endogenous Npt2B is at least reduced if not eliminated, where such animals also typically express an Npt2B peptide of the subject invention, e.g. the Npt2B protein of the subject invention or a fragment thereof. Where a nucleic acid having a sequence found in the human Npt2B gene is introduced, the introduced nucleic acid may be either a complete or partial sequence of the Npt2B gene. A detectable marker, such as lac Z may be introduced into the Npt2B locus, where upregulation of Npt2B expression will result in an easily detected change in phenotype. One may also provide for expression of the Npt2B gene or variants thereof in cells or tissues where it is not normally expressed, at levels not normally present in such cells or tissues.

DNA constructs for homologous recombination will comprise at least a portion of the Npt2B gene of the subject invention, wherein the gene has the desired genetic modification(s), and includes regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990), *Meth. Enzymol.* 185:527-537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on Npt2B activity.

Diagnostic Applications

Also provided are methods of diagnosing disease states based on observed levels of Npt2B or the expression level of the Npt2B gene in a biological sample of interest. Samples, as used herein, include biological fluids such as blood, cerebrospinal fluid, tears, saliva, lymph, dialysis fluid, semen and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

A number of methods are available for determining the expression level of a gene or protein in a particular sample. Diagnosis may be performed by a number of methods to determine the absence or presence or altered amounts of normal or abnormal Npt2B in a patient sample. For example, detection may utilize staining of cells or histological sections with labeled antibodies, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a fluorescent compound, e.g. fluorescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

Alternatively, one may focus on the expression of Npt2B. Biochemical studies may be performed to determine whether a sequence polymorphism in a Npt2B coding region or control regions is associated with disease. Disease associated polymorphisms may include deletion or truncation of the gene, mutations that alter expression level, that affect the activity of the protein, etc.

Changes in the promoter or enhancer sequence that may affect expression levels of Npt2B can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express Npt2B may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985), *Science* 239:487, and a review of techniques may be found in Sambrook, et al. *Molecular Cloning: A Laboratory Manual*, CSH Press 1989, pp.14.2-14.33. Alternatively, various methods are known in the art that utilize oligonucleotide ligation as a means of detecting polymorphisms, for examples see Riley et al. (1990), *Nucl. Acids Res.* 18:2887-2890; and Delahunty et al. (1996), *Am. J. Hum. Genet.* 58:1239-1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a wild-type Npt2B gene sequence. Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO 95/35505, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in Npt2B may be based on the functional or antigenic characteristics of the protein. Protein truncation assays are useful in detecting deletions that may affect the biological activity of the protein. Various immunoassays designed to detect polymorphisms in Npt2B proteins may be used in screening. Where many diverse genetic mutations lead to a particular disease phenotype, functional protein assays have proven to be effective screening tools. The activity of the encoded Npt2B protein may be determined by comparison with the wild-type protein.

Diagnostic methods of the subject invention in which the level of Npt2B gene expression is of interest will typically involve comparison of the Npt2B nucleic acid abundance of a sample of interest with that of a control value to determine any relative differences, where the difference may be measured qualitatively and/or quantitatively, which differences are then related to the presence or absence of an abnormal Npt2B gene expression pattern. A variety of different methods for determine the nucleic acid abundance in a sample are known to those of skill in the art, where particular methods of interest include those described in: Pietu et al., Genome Res. (June 1996) 6: 492-503; Zhao et al., Gene (Apr. 24, 1995) 156: 207-213; Soares, Curr. Opin. Biotechnol. (October 1997) 8: 542-546; Raval, J. Pharmacol Toxicol Methods (November 1994) 32: 125-127; Chalifour et al., Anal. Biochem (Feb. 1, 1994) 216: 299-304; Stolz & Tuan, Mol. Biotechnol. (December 19960 6: 225-230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

Screening Assays

The subject Npt2B polypeptides find use in various screening assays designed to identify therapeutic agents. Thus, one can use a cell model such as a host cell, e.g. CHO, HEK293, COS7, Xenopus Oocyte, etc., which has been transfected in a manner sufficient to express Npt2B on its surface. One can then contact the cell with a medium comprising sodium and phosphate ions, and measure the amount of phosphate anions that are internalized in the cell, where measurements are taken in both control environments and test environments, e.g. in the presence of a candidate Npt2B modulator compound, e.g. an Npt2B agonist or an Npt2B antagonist or inhibitor. To assist in detection of Pi uptake, labeled phosphorous is present in the medium, where any convenient label may be employed, such as an isotopic label, e.g. as present in $^{32}$P or $^{33}$P. Alternatively, current measurements may be taking using well known electrophysiological methods (see e.g. Electrophysiology, A practical Approach (IRL Press)(1993)), from which the uptake of Pi may be determined. Examples of assays for measuring Pi uptake are provided in: Maganin et al., Proc. Nat'l Acad. Sci USA (July 1993) 90: 5979-5983; and Helps et al., Eur. J. Biochem. (1995) 228: 927-930.

Also of interest in screening assays are non-human transgenic animals which express functional Npt2B, where such animals are described above. In many embodiments, the animals lack endogenous Npt2B. In using such animals for screening applications, a test compound(s) is administered to the animal, and the resultant changes in phenotype, e.g. serum Pi level, if any, are compared with a control.

Alternatively, in vitro models may be prepared and employed. For example, Npt2B binding activity may be measured in an in vitro environment in which binding events between Npt2B and candidate Npt2B modulatory agents are monitored. In yet other in vitro models, synthetic lipid bilayers incorporting the subject Npt2B cotransporter are prepared, an Pi passage from one side of the lipid bilayer to another is measured. Examples of such synthetic lipid bilayer assays can be found in: Brutyan et al., Biochimica et Biophysica Acta (1995) 1236:339-344; Wonderlin et al., Biophys. J. (1990) 58:289-297; and Suarez-Isla et al. Biochemistry (1983) 22:2319-2323.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used.

A variety of different candidate therapeutic agents that serve as either Npt2B agonists or antagonists may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Of particular interest in many embodiments are screening methods that identify agents that selectively modulate, e.g. inhibit, the subject Npt2B and not other sodium phosphate cotransporters, such as the renal sodium phosphate cotransporters, e.g. Npt1. To identify such agents, a multi step screening protocol can be performed, where agents that inhibit Npt2B in a first assay are then assayed for their ability to inhibit non-Npt2B transporters. Any convenient assay can be employed in this second step assay, such as those disclosed in Maganin et al., Proc. Nat'l Acad. Sci USA (July 1993) 90: 5979-5983; and Helps et al., Eur. J. Biochem. (1995) 228: 927-930.

Npt2B Nucleic Acid and Polypeptide Therapeutic Compositions

The nucleic acid compositions of the subject invention also find use as therapeutic agents in situations where one wishes to enhance Npt2B activity in a host, e.g. disease conditions associate with hypophosphatemia. The Npt2B genes, gene fragments, or the encoded Npt2B protein or protein fragments are useful in gene therapy to treat disorders associated with Npt2B defects. Expression vectors may be used to introduce the Npt2B gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or Npt2B protein may be introduced into tissues or host cells by any number of routes, including viral infection, microinjection, or fusion of vesicles. Jet injection may also be used for intramuscular administration, as described by Furth et al. (1992), *Anal Biochem* 205:365-368. The DNA may be coated onto gold microparticles, and delivered intradermally by a particle bombardment device, or "gene gun" as described in the literature (see, for example, Tang et al. (1992), *Nature* 356:152-154), where gold microprojectiles are coated with the DNA, then bombarded into skin cells.

Methods of Modulating Npt2B Activity

The subject invention provides methods of modulating Npt2B activity in a cell, including methods of increasing Npt2B activity (e.g. methods of enhancing Pi transport), as well as methods of reducing or inhibiting Npt2B activity, e.g. methods of stopping or limiting Pi transport. In such methods, an effective amount of an Npt2B modulatory agent is contacted with the cell.

Also provided are methods of modulating, including enhancing and inhibiting, Npt2B activity in a host. In such methods, an effective amount of active agent that modulates the activity of Npt2B in vivo, e.g. usually enhances or inhibits Npt2B activity, is administered to the host. The active agent may be a variety of different compounds, including a naturally occurring or synthetic small molecule compound, an antibody, fragment or derivative thereof, an antisense composition, and the like.

Of particular interest in certain embodiments are agents that reduce Npt2B activity, e.g. Pi transport, by at least about 10 fold, usually at least about 20 fold and more usually at least about 25 fold, as measure by the Oocyte Transport Assay as described in Magagnin, supra. In many embodiments, of particular interest is the use of compounds that reduce Npt2b activity by at least 100 fold, as compared to a control.

Also of interest is the use of agents that, while providing for reduced Npt2B activity, do not substantially reduce the activity of other sodium phosphate co-transporters, e.g. Npt1, etc., if at all. Thus, the agents in this embodiment are selective inhibitors of Npt2B. An agent is considered to be selective if it provides for the above reduced Npt2B activity, but substantially no reduced activity of at least one other type of sodium phosphate co-transporter, where substantially no means less than 10 fold reduction, usually less than 5 fold reduction and in many instances less than 1 fold reduction, where activity is measured as described in Magagnin, supra.

Naturally occurring or synthetic small molecule compounds of interest include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Also of interest as active agent are antibodies that at least reduce, if not inhibit, the target Npt2B activity in the host. Suitable antibodies are obtained by immunizing a host animal with peptides comprising all or a portion of the target protein, e.g. Npt2B. Suitable host animals include mouse, rat sheep, goat, hamster, rabbit, etc. The origin of the protein immunogen may be mouse, human, rat, monkey etc. The host animal will generally be a different species than the immunogen, e.g. human Npt2B used to immunize mice, etc.

The immunogen may comprise the complete protein, or fragments and derivatives thereof. Preferred immunogens comprise all or a part of Npt2B, where these residues contain the post-translation modifications, such as glycosylation, found on the native target protein. Immunogens comprising the extracellular domain are produced in a variety of ways known in the art, e.g. expression of cloned genes using conventional recombinant methods, isolation from HEC, etc.

For preparation of polyclonal antibodies, the first step is immunization of the host animal with the target protein, where the target protein will preferably be in substantially pure form, comprising less than about 1% contaminant. The immunogen may comprise the complete target protein, fragments or derivatives thereof. To increase the immune response of the host animal, the target protein may be combined with an adjuvant, where suitable adjuvants include alum, dextran, sulfate, large polymeric anions, oil & water emulsions, e.g. Freund's adjuvant, Freund's complete adjuvant, and the like. The target protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The target protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using Npt2B bound to an insoluble support, protein A sepharose, etc.

The antibody may be produced as a single chain, instead of the normal multimeric structure. Single chain antibodies are described in Jost et al. (1994) *J.B.C.* 269:26267-73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

For in vivo use, particularly for injection into humans, it is desirable to decrease the antigenicity of the antibody. An immune response of a recipient against the blocking agent will potentially decrease the period of time that the therapy is effective. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *P.N.A.S.* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, $F(ab')_2$ and Fab may be prepared by cleavage of the intact protein, e.g. by protease or chemical cleavage. Alternatively, a truncated gene is designed. For example, a chimeric gene encoding a portion of the $F(ab')_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, etc.

In yet other embodiments of the invention, the active agent is an agent that modulates, and generally decreases or down regulates, the expression of the gene encoding the target protein in the host. For example, antisense molecules can be used to down-regulate expression of Npt2B in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840-844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434-42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), *Appl. Biochem. Biotechnol.* 54:43-56.

As mentioned above, an effective amount of the active agent is administered to the host, where "effective amount" means a dosage sufficient to produce a desired result. Generally, the desired result is at least an enhancement or reduction in phosphate anion intestinal absorption, as measured by plasma Pi levels, as compared to a control.

In the subject methods, the active agent(s) may be administered to the host using any convenient means capable of resulting in the desired modulation of Npt2B activity, e.g. desired reduction in Pi absorption and plasma Pi levels. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of the agents can be achieved in various ways, including oral, buccal, rectal, parenteral, intraperitoneal, intradermal, transdermal, intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, e.g. antisense composition, it may be introduced into tissues or host cells by any number of routes, including viral infection, microinjection, or fusion of vesicles. Jet injection may also be used for intramuscular administration, as described by Furth et al. (1992), *Anal Biochem* 205:365-368. The DNA may be coated onto gold microparticles, and delivered intradermally by a particle bombardment device, or "gene gun" as described in the literature (see, for example, Tang et al. (1992), *Nature* 356:152-154), where gold microprojectiles are coated with the therapeutic DNA, then bombarded into skin cells.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

The subject methods find use in the treatment of a variety of different disease conditions involving Npt2B activity. As such, the disease conditions treatable according to the subject methods include diseases characterized by abnormally high Pi absorption and disease conditions characterized by abnormally low Pi absorption. Disease conditions resulting from abnormally low Npt2B activity are those characterized by the presence of hypophosphatemia, and include: osteomalacia, hypocalciurea, rickets, and the like. Disease conditions resulting from abnormally high Npt2B activity are those characterized by the presence of hyperphosphatemia and include: hyperparathyroidism, hypocalcemia, vitamin D deficiency, soft tissue or metastatic calcification, and the like. Of particular interest is the use of the subject methods to treat hyperphosphatemia resulting from renal insufficiency, e.g. caused by renal disease resulting in at least impaired renal function, and the like.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as hyperphosphatemia. As such, treatment also includes situations where the pathological condition, or at least symptoms associated therewith, are completely inhibited, e.g prevented from happening, or stopped, e.g. terminated, such that the host no longer suffers from the pathological condition, or at least the symptoms that characterize the pathological condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the active agent, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

The following examples are offered primarily for purposes of illustration. It will be readily apparent to those skilled in the art that the formulations, dosages, methods of administration, and other parameters of this invention may be further modified or substituted in various ways without departing from the spirit and scope of the invention.

Experimental

A. Identification of the Npt2B Sequence

Comparison of type II sodium-phosphate cotransporter protein sequences from different species available from public databases revealed that whilst most were very closely related, the bovine and flounder sequences appeared to form a distinct sub-family. The Incyte LifeSeq database was thus searched for Npt2-like clones that more closely resembled the bovine sequence than they did the human. A number of clones were identified and three of them were obtained and the DNA sequence of the entire inserts determined. DNA sequencing was performed on an automated sequencer (PE/Applied Biosystems Model 373A, Foster City, Calif.) using vendor's dye dideoxy termination sequencing kit. Comparison of the sequences revealed that they represented the same cDNA and that the longest was only a partial clone missing approximately 150 amino acids from the N-terminus, based on homology to the bovine protein. The consensus sequence was used to further screen the LifeSeq database and a large number of clones were identified, including one which appeared to contain the full-length coding sequence. The latter was obtained from Incyte and sequenced. This revealed the presence of a 689 amino acid open reading frame which appeared to be a human member of the bovine/flounder type II cotransporter subfamily. The majority of the clones identified in the LifeSeq database were from libraries derived from lung-related tissue samples, however some of the clones were from libraries of small intestine and ovarian origin. This suggested that this cDNA might be a candidate for the human intestinal sodium-phosphate cotransporter. Experiments using RT-PCR confirmed the expression of this gene in cDNA derived from human small intestine samples (obtained from Clontech Corporation, Palo Alto, Calif.). Subsequently, assignment of this sequence as the human intestinal transporter was strengthened by a high degree of homology to published sequences for Xenopus (A. Ishizuya-Oka et al. (1997) Temporal and Spatial Expression of an Intestinal $Na^+/PO_4^{3-}$ Cotransporter Correlates With Epithelial Transformation During Thyroid Hormone-Dependent Frog Metamorphosis. Develoment Genetics 20:53-66) and mouse (H. Hilfiker et al., Characterization of a murine type II sodium-phosphate cotransporter expressed in mammalian small intestine. PNAS 1998 95: 14564-14569) intestinal transporters.

B. Expression in Mammalian Cells and Assay Protocol for Na/Pi Transporter

The Human Npt2B cDNA is cloned into a suitable constitutive mammalian expression vector such as pcDNA3.1 or pREP9 (both from Invitrogen, Carlsbad, Calif.). If required, the cDNA is cloned into an inducible vector such as pLK-neo, a glucocorticoid-inducible vector (from Prof. Nicholas Fasel, Institute of Biochemistry, University of Lausanne, Switzerland; as described in Gene, 111, 199-206 (1992)). A number of mammalian cell lines, e.g. HEK 293, CHO, MDCK, BHK and NIH 3T3 are transfected with the expression constructs, and screened for stable expression of the recombinant transporter using a version of the assay described below.

Cells expressing the transporter are plated in 96 well tissue culture plates at 50,000 to 100,000 cells per well in 200 μl of suitable media and allowed to adhere for 3-16 hours. Immediately before the assay, cells are washed three times with sodium- and phosphate-free wash buffer (137 mM N-methyl-D-glucamine, 5.4 mM KCl, 2.8 mM $CaCl_2$, 1.2 mM $MgCl_2$, 10 mM HEPES, pH adjusted to 7.4 with HCl). The following components are then added, (1) 50 μl of reaction buffer (137 mM NaCl, 5.4 mM KCl, 2.8 mM $CaCl_2$, 1.2 mM $MgCl_2$, 0.1 mM $kH_2PO4$, 10 mM HEPES, pH adjusted to 7.4 with KOH), (2) 40 μl of test compounds diluted in reaction buffer and (3) 10 μl of a 10×phosphate solution (final concentration of phosphate is 100 μM) containing either $^{32}P$ (0.25 μCi) or $^{33}P$ (0.5 μCi) as tracer. Plates are incubated at room temperature for 20-30 minutes, and the reaction is stopped by removing the uptake solution and washing the cells 3 times with ice-cold stop solution (137 mM NaCl, 10 mM Tris-HCl, pH 7.2). The radioactivity taken up by the cells is determined by counting after the addition of 150 μl of scintillation cocktail. Controls consist of cells incubated without test compound (vehicle alone) and cells incubated with N-methyl-D-glucamine in the reaction buffer instead of sodium. Inhibitory activity is expressed as percentage inhibition of sodium-dependent uptake of the tracer. Using the above protocol, candidate therapeutic agents are screened for their Npt2B modulatory activity.

It is apparent from the above results and discussion that a novel human intestinal sodium phosphate cotransporter, as well as polypeptides related thereto and nucleic acid compositions encoding the same, are provided by the subject invention. These polypeptide and nucleic acid compositions find use in a variety of diverse applications, including research, diagnostic, screening and therapeutic applications. Also provided are novel methods of treating diseases associated abnormalities in plasma phosphate levels, as the identification of the subject sodium phosphate cotransporter provides for an additional target for therapeutic agents for such diseases. Accordingly, the subject invention provides for a significant contribution to the field.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. An isolated Npt2B polypeptide comprising the amino acid sequence set forth in SEQ ID NO: 1.

* * * * *

SEQUENCE LISTING

<160> NUMBER OF SEQ ID NOS: 2

<210> SEQ ID NO 1
<211> LENGTH: 689
<212> TYPE: PRT
<213> ORGANISM: human

<400> SEQUENCE: 1

Met Ala Pro Trp Pro Glu Leu Gly Asp Ala Gln Pro Asn Pro Asp Lys
 1               5                  10                  15

Tyr Leu Glu Gly Ala Ala Gly Gln Gln Pro Thr Ala Pro Asp Lys Ser
            20                  25                  30

Lys Glu Thr Asn Lys Asn Thr Glu Ala Pro Val Thr Lys Ile Glu
            35                  40                  45

-continued

```
Leu Leu Pro Ser Tyr Ser Thr Ala Thr Leu Ile Asp Glu Pro Thr Glu
     50                  55                  60

Val Asp Asp Pro Trp Asn Leu Pro Thr Leu Gln Asp Ser Gly Ile Lys
 65                  70                  75                  80

Trp Ser Glu Arg Asp Thr Lys Gly Lys Ile Leu Cys Phe Phe Gln Gly
                 85                  90                  95

Ile Gly Arg Leu Ile Leu Leu Leu Gly Phe Leu Tyr Phe Phe Val Cys
             100                 105                 110

Ser Leu Asp Ile Leu Ser Ser Ala Phe Gln Leu Val Gly Gly Lys Met
         115                 120                 125

Ala Gly Gln Phe Phe Ser Asn Ser Ser Ile Met Ser Asn Pro Leu Leu
     130                 135                 140

Gly Leu Val Ile Gly Val Leu Val Thr Val Leu Val Gln Ser Ser Ser
145                 150                 155                 160

Thr Ser Thr Ser Ile Val Val Ser Met Val Ser Ser Leu Leu Thr
                 165                 170                 175

Val Arg Ala Ala Ile Pro Ile Ile Met Gly Ala Asn Ile Gly Thr Ser
             180                 185                 190

Ile Thr Asn Thr Ile Val Ala Leu Met Gln Val Gly Asp Arg Ser Glu
         195                 200                 205

Phe Arg Arg Ala Phe Ala Gly Ala Thr Val His Asp Phe Phe Asn Trp
     210                 215                 220

Leu Ser Val Leu Val Leu Leu Pro Val Glu Val Ala Thr His Tyr Leu
225                 230                 235                 240

Glu Ile Ile Thr Gln Leu Ile Val Glu Ser Phe His Phe Lys Asn Gly
                 245                 250                 255

Glu Asp Ala Pro Asp Leu Leu Lys Val Ile Thr Lys Pro Phe Thr Lys
             260                 265                 270

Leu Ile Val Gln Leu Asp Lys Lys Val Ile Ser Gln Ile Ala Met Asn
         275                 280                 285

Asp Glu Lys Ala Lys Asn Lys Ser Leu Val Lys Ile Trp Cys Lys Thr
     290                 295                 300

Phe Thr Asn Lys Thr Gln Ile Asn Val Thr Val Pro Ser Thr Ala Asn
305                 310                 315                 320

Cys Thr Ser Pro Ser Leu Cys Trp Thr Asp Gly Ile Gln Asn Trp Thr
                 325                 330                 335

Met Lys Asn Val Thr Tyr Lys Glu Asn Ile Ala Lys Cys Gln His Ile
             340                 345                 350

Phe Val Asn Phe His Leu Pro Asp Leu Ala Val Gly Thr Ile Leu Leu
         355                 360                 365

Ile Leu Ser Leu Leu Val Leu Cys Gly Cys Leu Ile Met Ile Val Lys
     370                 375                 380

Ile Leu Gly Ser Val Leu Lys Gly Gln Val Ala Thr Ile Lys Lys
385                 390                 395                 400

Thr Ile Asn Thr Asp Phe Pro Phe Pro Phe Ala Trp Leu Thr Gly Tyr
                 405                 410                 415

Leu Ala Ile Leu Val Gly Ala Gly Met Thr Phe Ile Val Gln Ser Ser
             420                 425                 430

Ser Val Phe Thr Ser Ala Leu Thr Pro Leu Ile Gly Ile Gly Val Ile
         435                 440                 445

Thr Ile Glu Arg Ala Tyr Pro Leu Thr Leu Gly Ser Asn Ile Gly Thr
     450                 455                 460

Thr Thr Thr Ala Ile Leu Ala Ala Leu Ala Ser Pro Gly Asn Ala Leu
```

```
                465            470            475            480

Arg Ser Ser Leu Gln Ile Ala Leu Cys His Phe Phe Asn Ile Ser
                485                       490                       495

Gly Ile Leu Leu Trp Tyr Pro Ile Pro Phe Thr Arg Leu Pro Ile Arg
                500                       505                       510

Met Ala Lys Gly Leu Gly Asn Ile Ser Ala Lys Tyr Arg Trp Phe Ala
                515                       520                       525

Val Phe Tyr Leu Ile Ile Phe Phe Leu Ile Pro Leu Thr Val Phe
            530                       535                       540

Gly Leu Ser Leu Ala Gly Trp Arg Val Leu Val Gly Val Gly Val Pro
545                       550                       555                       560

Val Val Phe Ile Ile Ile Leu Val Leu Cys Leu Arg Leu Leu Gln Ser
                        565                       570                       575

Arg Cys Pro Arg Val Leu Pro Lys Lys Leu Gln Asn Trp Asn Phe Leu
                580                       585                       590

Pro Leu Trp Met Arg Ser Leu Lys Pro Trp Asp Ala Val Val Ser Lys
            595                       600                       605

Phe Thr Gly Cys Phe Gln Met Arg Cys Cys Cys Cys Arg Val Cys
            610                       615                       620

Cys Arg Ala Cys Cys Leu Leu Cys Gly Cys Pro Lys Cys Cys Arg Cys
625                       630                       635                       640

Ser Lys Cys Cys Glu Asp Leu Glu Glu Ala Gln Gly Gln Asp Val
                        645                       650                       655

Pro Val Lys Ala Pro Glu Thr Phe Asp Asn Ile Thr Ile Ser Arg Glu
            660                       665                       670

Ala Gln Gly Glu Val Pro Ala Ser Asp Ser Lys Thr Glu Cys Thr Ala
            675                       680                       685

Leu

<210> SEQ ID NO 2
<211> LENGTH: 4137
<212> TYPE: DNA
<213> ORGANISM: human

<400> SEQUENCE: 2
ctgacgtagg cccagcacct gcggagggag cgctgaccat ggctccctgg cctgaattgg    60
gagatgccca gcccaacccc gataagtacc tcgaaggggc cgcaggtcag cagcccactg   120
cccctgataa aagcaaagag accaacaaaa ataacactga ggcacctgta accaagattg   180
aacttctgcc gtcctactcc acggctacac tgatagatga gcccactgag gtggatgacc   240
cctggaacct acccactctt caggactcgg ggatcaagtg gtcagagaga gacaccaaag   300
ggaagattct ctgtttcttc caagggattg ggagattgat tttacttctc ggatttctct   360 acttttttcgt gtgctccctg gatattctta gtagcgcctt ccagctggtt ggaggaaaaa   420
tggcaggaca gttcttcagc aacagctcta ttatgtccaa ccctttgttg gggctggtga   480
tcggggtgct ggtgaccgtc ttggtgcaga gctccagcac ctcaacgtcc atcgttgtca   540
gcatggtgtc ctcttcattg ctcactgttc gggctgccat ccccattatc atggggcca   600 acattggaac gtcaatcacc aacactattg ttgcgctcat gcaggtggga gatcggagtg   660
agttcagaag agcttttgca ggagccactg tccatgactt cttcaactgg ctgtccgtgt   720
tggtgctctt gccgtggag gtggccaccc attacctcga gatcataacc cagcttatag   780
tggagagctt ccacttcaag aatggagaag atgccccaga tcttctgaaa gtcatcacta   840
```

```
agcccttcac aaagctcatt gtccagctgg ataaaaaagt tatcagccaa attgcaatga    900
acgatgaaaa agcgaaaaac aagagtcttg tcaagatttg gtgcaaaact tttaccaaca    960
agacccagat taacgtcact gttccctcga ctgctaactg cacctcccct tccctctgtt   1020
ggacggatgg catccaaaac tggaccatga agaatgtgac ctacaaggag aacatcgcca   1080
aatgccagca tatctttgtg aatttccacc tcccggatct tgctgtgggc accatcttgc   1140
tcatactctc cctgctggtc ctctgtggtt gcctgatcat gattgtcaag atcctgggct   1200
ctgtgctcaa ggggcaggtc gccactgtca tcaagaagac catcaacact gatttcccct   1260
ttccctttgc atggttgact ggctacctgg ccatcctcgt cggggcaggc atgaccttca   1320
tcgtacagag cagctctgtg ttcacgtcgg ccttgacccc cctgattgga atcggcgtga   1380
taaccattga gagggcttat ccactcacgc tgggctccaa catcggcacc accaccaccg   1440
ccatcctggc cgccttagcc agccctggca atgcattgag gagttcactc cagatcgccc   1500
tgtgccactt ttcttcaac atctccggca tcttgctgtg gtacccgatc ccgttcactc   1560
gcctgcccat ccgcatggcc aaggggctgg gcaacatctc tgccaagtat cgctggttcg   1620
ccgtcttcta cctgatcatc ttcttcttcc tgatcccgct gacggtgttt ggcctctcgc   1680
tggccggctg gcgggtgctg gttggtgtcg gggttcccgt cgtcttcatc atcatcctgg   1740
tactgtgcct ccgactcctg cagtctcgct gcccacgcgt cctgccgaag aaactccaga   1800
actggaactt cctgccgctg tggatgcgct cgctgaagcc ctgggatgcc gtcgtctcca   1860
agttcaccgg ctgcttccag atgcgctgct gctgctgctg ccgcgtgtgc tgccgcgcgt   1920
gctgcttgct gtgtggctgc ccaagtgct gccgctgcag caagtgctgc gaggacttgg   1980
aggaggcgca ggaggggcag gatgtccctg tcaaggctcc tgagaccttt gataacataa   2040
ccattagcag agaggctcag ggtgaggtcc ctgcctcgga ctcaaagacc gaatgcacgg   2100
ccttgtaggg gacgcccag attgtcaggg atgggggat ggtccttgag ttttgcatgc   2160
tctcctccct cccacttctg caccctttca ccacctcgag gagatttgct ccccattagc   2220
gaatgaaatt gatgcagtcc tacctaactc gattcccttt ggcttggtgg gtaggcctgc   2280
agggcacttt tattccaacc cctggtcact cagtaatctt ttactccagg aaggcacagg   2340
atggtaccta aagagaatta gagaatgaac ctggcgggac ggatgtctaa tcctgcacct   2400
agctgggttg gtcagtagaa cctatttca gactcaaaaa ccatcttcag aaagaaaagg   2460
cccagggaag gaatgtatga gaggctctcc cagatgagga agtgtactct ctatgactat   2520
caagctcagg cctctcccctt ttttaaacc aaagtctggc aaccaagagc agcagctcca   2580
tggcctcctt gccccagatc agcctgggtc aggggacata gtgtcattgt ttggaaactg   2640
cagaccacaa ggtgtgggtc tatcccactt cctagtgctc cccacattcc ccatcagggc   2700
ttcctcacgt ggacaggtgt gctagtccag gcagttcact tgcagtttcc ttgtcctcat   2760
gcttcgggga tgggagccac gcctgaacta gagttcaggc tggatacatg tgctcacctg   2820
ctgctcttgt cttcctaaga gacagagagt ggggcagatg gaggagaaga aagtgaggaa   2880
tgagtagcat agcattctgc caaaagggcc ccagattctt aatttagcaa actaagaagc   2940
ccaattcaaa agcattgtgg ctaaagtcta acgctcctct cttggtcaga taacaaaagc   3000
cctccctgtt ggatctttg aaataaaacg tgcaagttat ccaggctcgt agcctgcatg   3060
ctgccacctt gaatcccagg gagtatctgc acctggaata gctctccacc cctctctgcc   3120
tccttacttt ctgtgcaaga tgacttcctg ggttaacttc cttctttcca tccacccacc   3180
cactggaatc tctttccaaa cattttttcca ttttcccaca gatgggcttt gattagctgt   3240
```

```
cctctctcca tgcctgcaaa gctccagatt tttggggaaa gctgtaccca actggactgc    3300
ccagtgaact gggatcattg agtacagtcg agcacacgtg tgtgcatggg tcaaaggggt    3360
gtgttccttc tcatcctaga tgccttctct gtgccttcca cagcctcctg cctgattaca    3420
ccactgcccc cgccccaccc tcagccatcc caattcttcc tggccagtgc gctccagcct    3480
tatctaggaa aggaggagtg ggtgtagccg tgcagcaaga ttggggcctc ccccatccca    3540
gcttctccac catcccagca agtcaggata tcagacagtc ctccctgac cctcccctt     3600 gtagatatca attcccaaac agagccaaat actctatatc tatagtcaca gccctgtaca    3660 gcattttca taagttatat agtaaatggt cttctagtgc tctcatttgg aaatgaggca     3720
ggcttcttct atgaaatgta aagaaagaaa ccactttgta tattttgtaa taccacctct    3780
gtggccatgc ctgccccgcc cactctgtat atatgtaagt taaacccggg caggggctgt    3840
ggccgtcttt gtactctggt gatttttaga aattgaatct ttgtacttgc attgattgta    3900
taataatttt gagaccaggt ctcgctgtgt tgctcaggct ggtctcaaac tcctgagatc    3960
aagcaatccg cccacctcag cctcccaaag tgctgagatc acaggcgtga gccaccacca    4020
ggcctgattg taattttttt tttttttttt tttactggtt atgggaaggg agaaataaaa    4080
tcatcaaacc caaaaaaaaa aaaaaaaaaa aaaaaaaaaa aaaaaaaaaa aaaaaaa      4137
```